| (12) United States Patent<br>Finkel et al. | (10) Patent No.: US 9,387,231 B2<br>(45) Date of Patent: Jul. 12, 2016 |
|---|---|

(54) COMPOSITIONS COMPRISING A BRD4 ANTAGONIST AND METHODS FOR THE TREATMENT OF HIV

(71) Applicant: THE CHILDREN'S HOSPITAL OF PHILADELPHIA, Philadelphia, PA (US)

(72) Inventors: Terri H. Finkel, Orlando, FL (US); Jiangfang Wang, Orlando, FL (US); Gerd Blobel, Bala Cynwyd, PA (US); Stephan Kadauke, Brookline, MA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/167,372

(22) Filed: Jan. 29, 2014

(65) Prior Publication Data

US 2014/0199260 A1 Jul. 17, 2014

Related U.S. Application Data

(63) Continuation-in-part of application No. PCT/US2012/048809, filed on Jul. 30, 2012.

(60) Provisional application No. 61/513,200, filed on Jul. 29, 2011.

(51) Int. Cl.
| A61K 38/17 | (2006.01) |
| A61K 45/06 | (2006.01) |
| A61K 31/4745 | (2006.01) |
| A61K 31/5517 | (2006.01) |
| A61K 38/19 | (2006.01) |
| A61K 38/20 | (2006.01) |
| A61K 38/16 | (2006.01) |

(52) U.S. Cl.
CPC ............. *A61K 38/17* (2013.01); *A61K 31/4745* (2013.01); *A61K 31/5517* (2013.01); *A61K 38/162* (2013.01); *A61K 38/191* (2013.01); *A61K 38/2046* (2013.01); *A61K 45/06* (2013.01)

(58) Field of Classification Search
None
See application file for complete search history.

(56) References Cited

U.S. PATENT DOCUMENTS

| 2009/0062355 A1 | 3/2009 | Iizawa et al. |
| 2010/0166806 A1 | 7/2010 | Castor |
| 2011/0117193 A1 | 5/2011 | Adeyeye et al. |
| 2012/0028912 A1 | 2/2012 | Zhou et al. |

FOREIGN PATENT DOCUMENTS

| WO | 2005/002526 | 1/2005 |
| WO | 2006/083692 | 8/2006 |
| WO | 2009/020559 | 2/2009 |
| WO | 2012151512 | 11/2012 |

OTHER PUBLICATIONS

Urano, E., et al., "Identification of the P-TEFb Complex-interacting Domain of Brd4 as an Inhibitor of HIV-1 Replication by Functional cDNA Library Screening in MT-4 Cells," FEBS Letters (2008) 582(29):4053-4058.
Weidner-Glunde, M., et al., "What do viruses BET on?," Frontiers in Bioscience (2010) 15:537-549.
Boehm, D., et al., "BET bromodomain-targeting compounds reactivate HIV from latency via a Tat-independent mechanism," Cell Cycle (2013) 12(3):452-462.
Bisgrove et al., "Conserved P-TEFb-Interacting Domain of BRD4 Inhibits HIV Transcription", PNAS, vol. 104, No. 34, pp. 13690-13695 (2007).
Filippakopoulos et al., Selective Inhibition of BET Bromodomains, Nature, vol. 468(7327), pp. 1067-1073 (2010).
Chung et al., "Discovery and Characterization of Small Molecule Inhibitors of the BET Family Bromodomains", J. Med. Chem., vol. 54, pp. 3827-3838 (2011).
Nicodeme, et al., "Suppression of Inflammation by a Synthetic Histone Mimic," Nature (2010) 468:1119-1123.
Vollmuth, et al., "Structures of the Dual Bromodomains of the P-TEFb-activating Protein Brd4 at Atomic Resolution," J. Biol. Chem. (2009) 284(52):36547-36556.
Wang, et al., "HIV-1 Vif Promotes the G1- to S-phase Cell-Cycle Transition," Blood (2011) 117(4):1260-1269.

*Primary Examiner* — Nicole Kinsey White
(74) *Attorney, Agent, or Firm* — Robert C. Netter, Jr.; Dann, Dorfman, Herrell & Skillman

(57) ABSTRACT

Compositions and methods for the treatment of HIV are provided.

18 Claims, 18 Drawing Sheets

A

B

C

US 9,387,231 B2

COMPOSITIONS COMPRISING A BRD4 ANTAGONIST AND METHODS FOR THE TREATMENT OF HIV

Figure 1A:
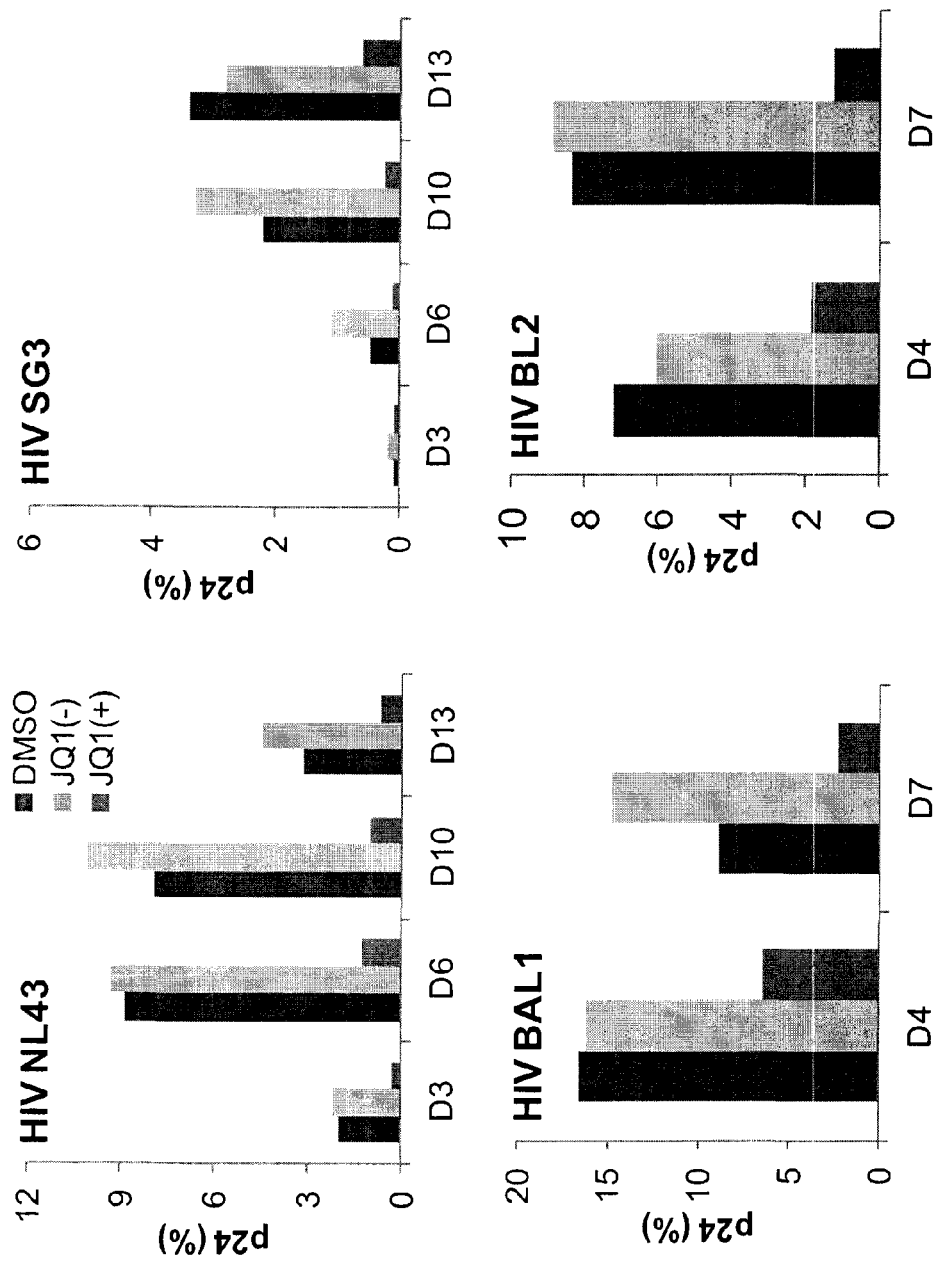

This application is a continuation-in-part of PCT/US2012/048809, filed on Jul. 30, 2012, which claims priority under 35 U.S.C. §119(e) to U.S. Provisional Patent Application No. 61/513,200, filed Jul. 29, 2011. The foregoing applications are incorporated by reference herein.

FIELD OF THE INVENTION

The present invention relates to the field of HIV therapy. More specifically, the invention provides methods and compositions for the treatment, inhibition, prevention, and/or cure of an HIV infection.

BACKGROUND OF THE INVENTION

One persistent obstacle to treating HIV infection is the ability of virus to enter a latent state, inaccessible to current antiretroviral (ARV) therapy. How HIV enters latency and remains latent is only partially understood. One theory is that changes in chromatin structure, such as histone deacetylation, suppress transcription from the HIV long terminal repeat (LTR), resulting in the establishment of latency. IL-7, prostratin, and histone deacetylase inhibitors have been tested to purge HIV from the latently infected reservoir. However, no appreciable decrease of the latent reservoir is observed when these drugs are combined with ARVs. In contrast to reactivating latent provirus, a drug that blocks cellular activation might reduce the initial burst of viremia and limit establishment of the latent viral reservoir. Cyclosporin A (CSA), an immunosuppressive agent, has been shown to suppress viral replication and restore normal CD4 T-cell levels. However, adverse effects of CSA advocate against its use in HIV disease. Development of new approaches to purge the HIV reservoir and prevent establishment of latency are critical therapeutic challenges.

SUMMARY OF THE INVENTION

In accordance with one aspect of the instant invention, methods for treating, inhibiting, and/or preventing a retroviral infection (e.g., HIV) in an animal are provided. In a particular embodiment, the method comprises administering to the subject at least one BET antagonist/inhibitor (e.g., in a pharmaceutically acceptable carrier). In a particular embodiment, the BET antagonist is a Brd4 antagonist. In yet another embodiment, the BET antagonist is a small molecule, particularly one that specifically binds the acetylated lysine recognition pocket/binding site of the BET (see, e.g., Filippakopoulos et al. (2010) Nature 468:1067-1073). The methods may further comprise the administration of at least one additional anti-retroviral (e.g., an anti-HIV) compound before, after, and/or simultaneously with the BET antagonist(s).

In accordance with another aspect of the instant invention, methods for inhibiting and/or preventing a retroviral (e.g., HIV) infection are provided. In a particular embodiment, the method comprises delivering to a cell at least one BET antagonist. In a particular embodiment, the BET antagonist is a Brd4 antagonist. In yet another embodiment, the BET antagonist is a small molecule, particularly one that specifically binds the acetylated lysine recognition pocket of the BET. The methods may further comprise the delivery of at least one anti-retroviral (e.g., an anti-HIV) compound before, after, and/or simultaneously with the BET antagonist(s).

In accordance with still another aspect of the instant invention, methods for inducing retroviral (e.g., HIV) reactivation are provided. In a particular embodiment, the method comprises delivering (e.g., contacting) at least one BET antagonist to a cell which is latently infected. In a particular embodiment, the BET antagonist is a Brd4 antagonist. In yet another embodiment, the BET antagonist is a small molecule, particularly one that specifically binds the acetylated lysine recognition pocket of the BET. The methods may further comprise the delivery of at least one additional anti-retroviral (e.g., an anti-HIV) compound before, after, and/or simultaneously with the BET antagonist(s).

According to another aspect of the instant invention, a composition comprising at least one BET antagonist, at least one additional anti-retroviral (e.g., an anti-HIV) and/or activation agent, and at least one pharmaceutically acceptable carrier are provided.

BRIEF DESCRIPTIONS OF THE DRAWING

Figure 1B:
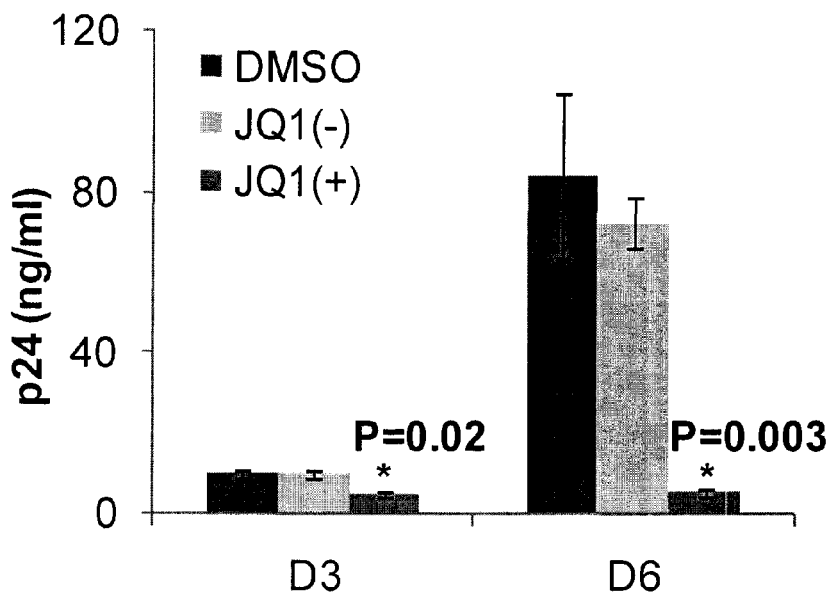
Figure 1C:
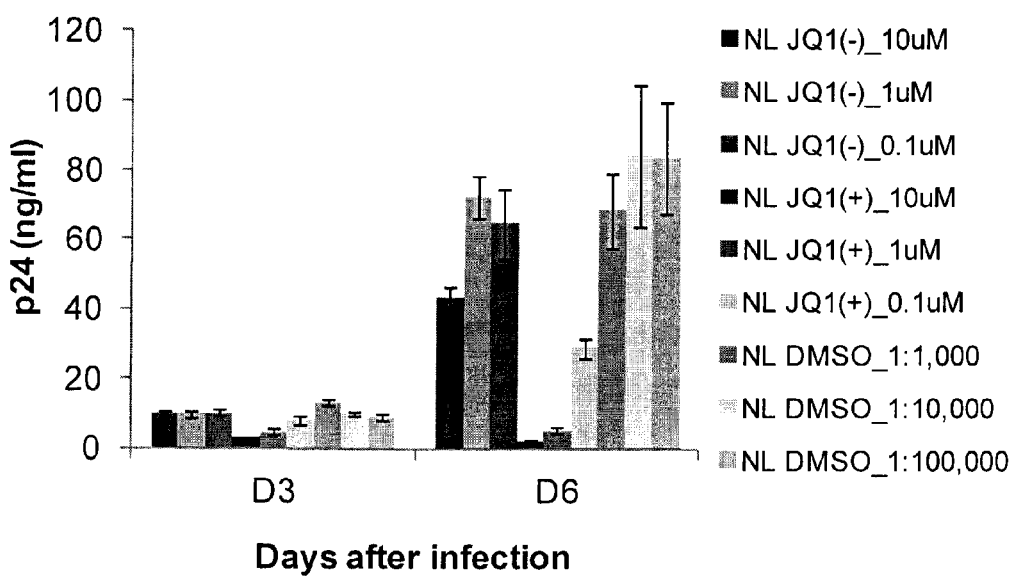
Figure 1D:
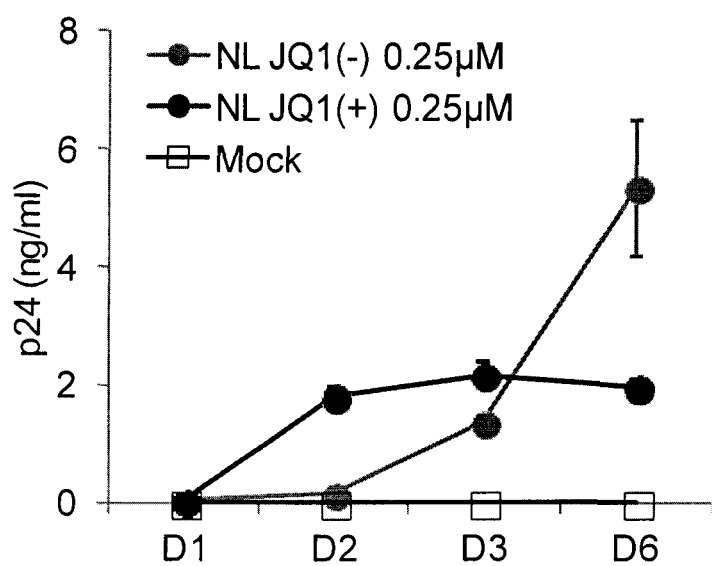

FIGS. 1A-1D provides graphs demonstrating that JQ1 inhibits HIV infection in primary CD4 T-cells. Primary CD4 T-cells were activated with anti-CD3/28, infected with NL43, SG3, BAL1, or BL2 (FIG. 1A) or NL43 (FIGS. 1B and 1C), and cultured in the presence of the BET antagonist JQ1(+) or the control enantiomer JQ1(−). FIG. 1A provides the expression of p24Gag in cells as determined by flow cytometry. FIGS. 1B and 1C show viral production as measured in culture supernatants by ELISA. FIG. 1C shows viral production with varying amounts of JQ1(+), JQ1(−), or the carrier dimethyl sulfoxide (DMSO). FIG. 1D shows the soluble p24 in the culture supernatants by ELISA in CEMss LTR-GFP cells infected with HIV NL4-3, in the presence of JQ1(+) (0.25 µM) or JQ1(−).

Figure 2A:
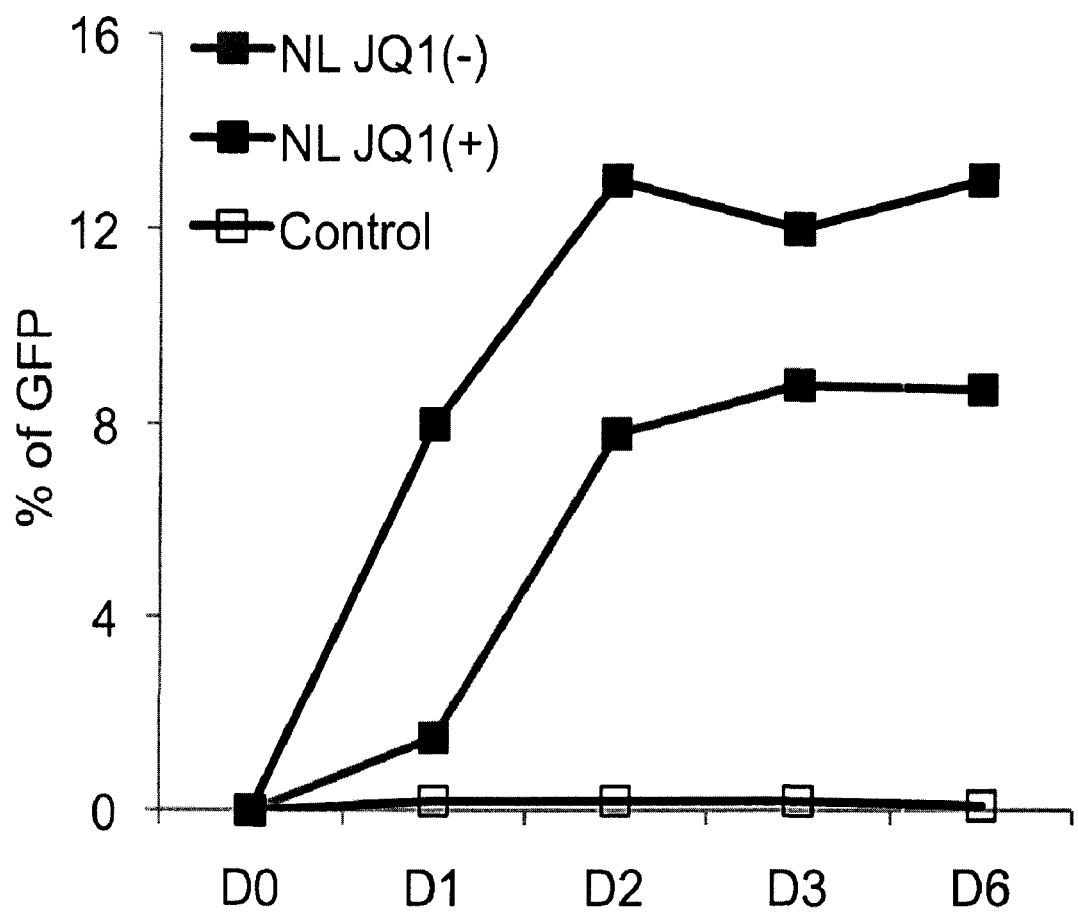
Figure 2B:
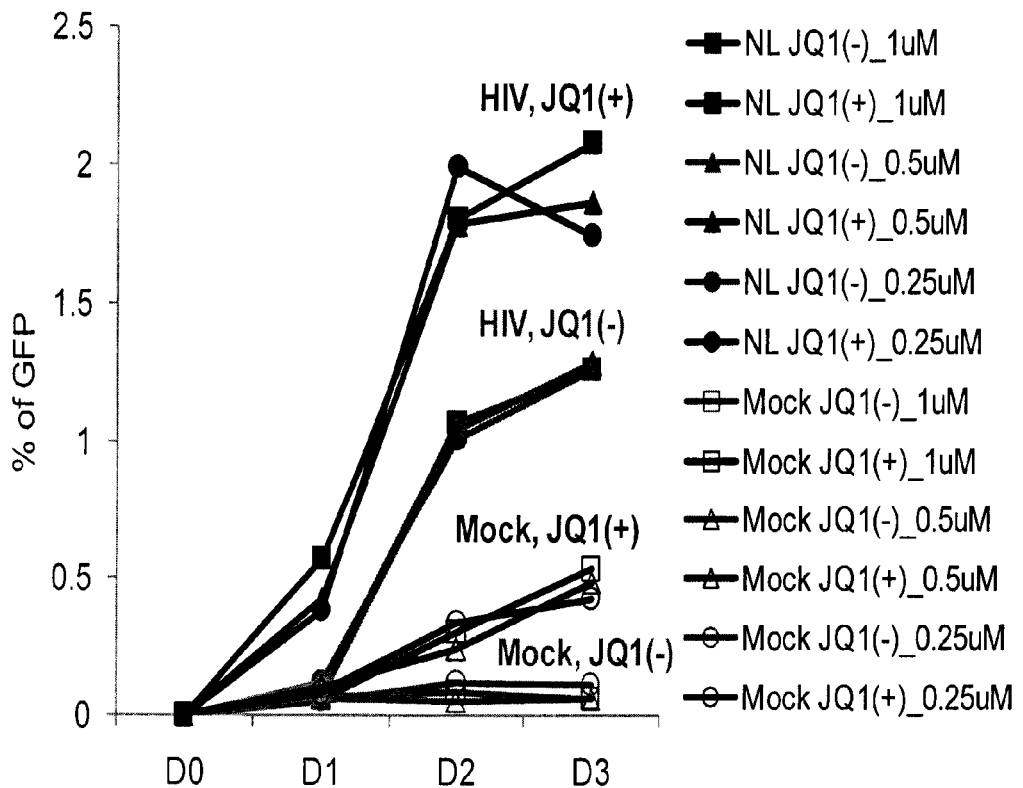
Figure 2C:
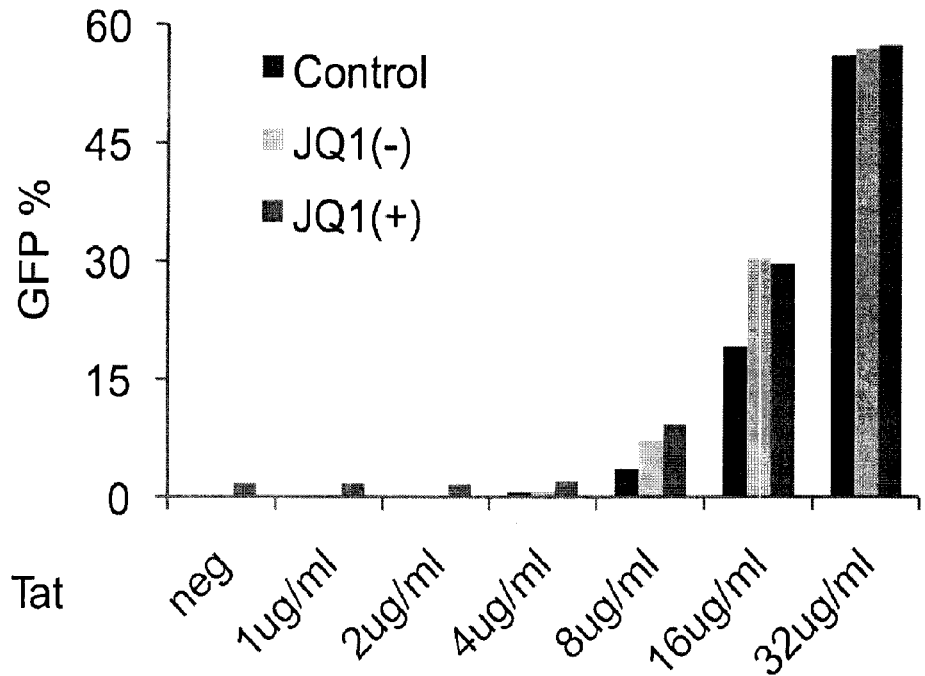
Figure 2D:
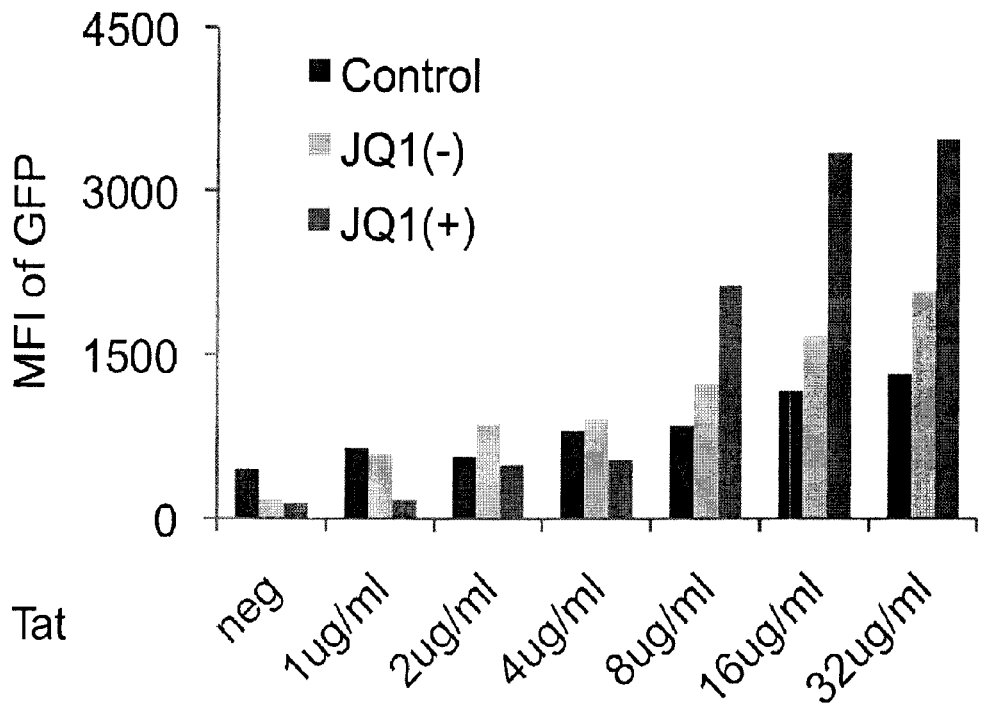
Figure 2E:
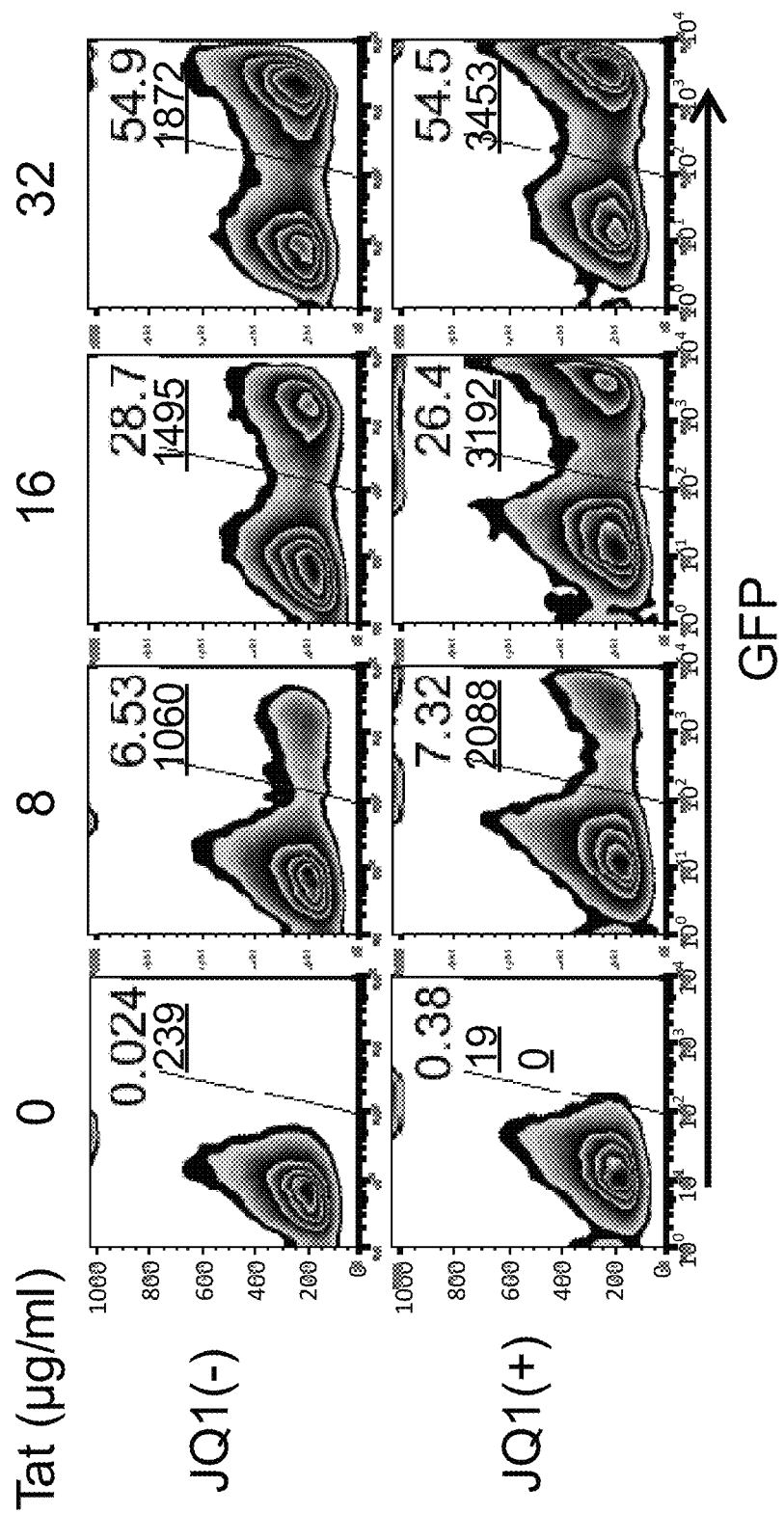

FIG. 2A shows that JQ1 drives activation of the HIV LTR. CEMss LTR-GFP cells were infected with NL43 and cultured in the presence of the BET antagonists JQ1(+) (1 µM) or the control enantiomer JQ1(−). GFP expression in cells was examined by flow cytometry. A representative of three experiments is shown. FIG. 2B provides a graph showing GFP expression in cells when cultured with different amounts of JQ1, as determined by flow cytometry. 0.25 µM of JQ1(+) was sufficient to dramatically increase the expression of GFP in NL43 infected CEMss LTR-GFP cells. FIGS. 2C and 2D show percentage of GFP expression (FIG. 2C) and mean fluorescence of GFP (MFI; FIG. 2D) in CEMss LTR-GFP cells cultured in the presence of JQ1(+) or JQ1(−) (1 µM), and different amount of HIV-1 Tat. FIG. 2E provides dot plots of CEMss LTR-GFP cells were cultured with increasing amounts of HIV Tat (0, 8, 16 or 32 µg/ml) in the presence of JQ1(+) or JQ1(−) (1 µM) for 1 day. Non-underlined numbers indicate percentage of GFP and underlined numbers indicate mean fluorescence of GFP (MFI).

Figure 3A:
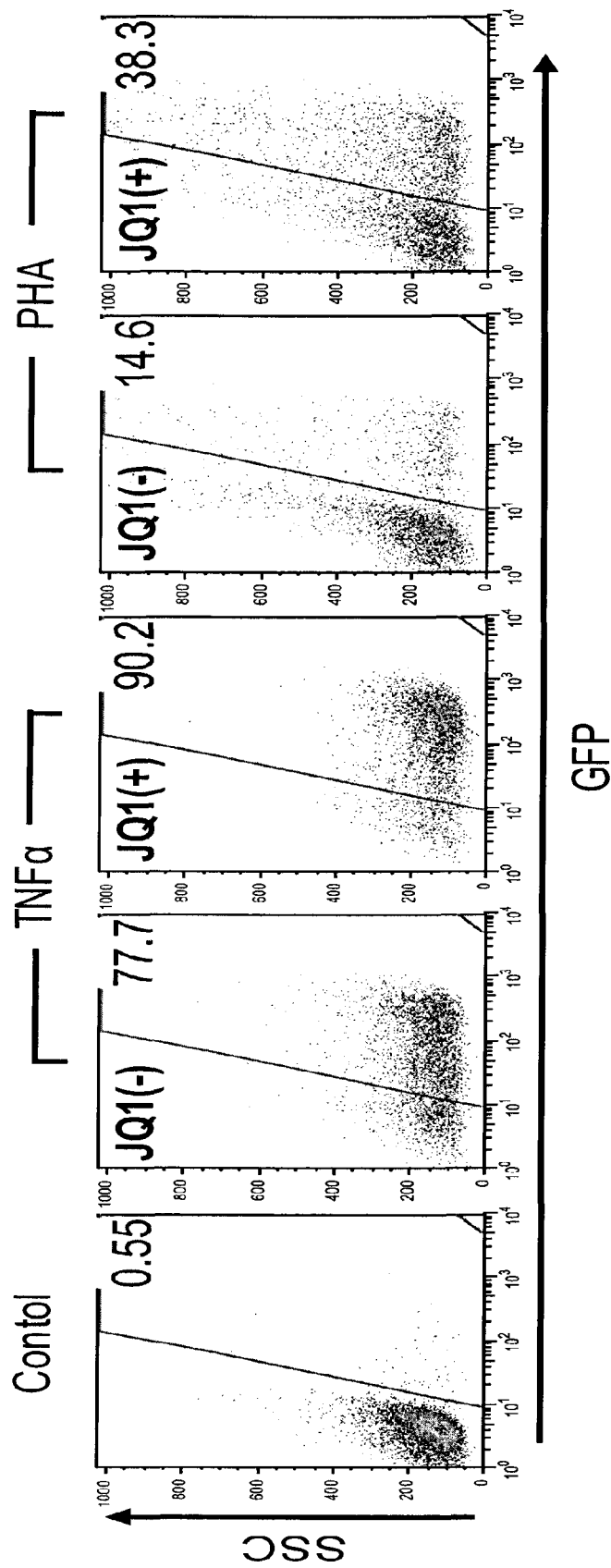
Figure 3B:
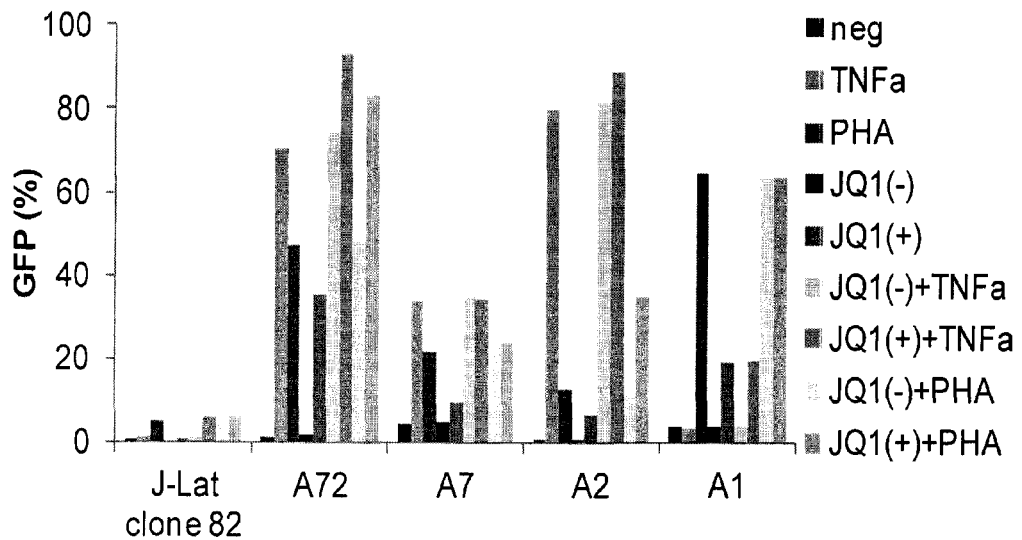
Figure 3C:
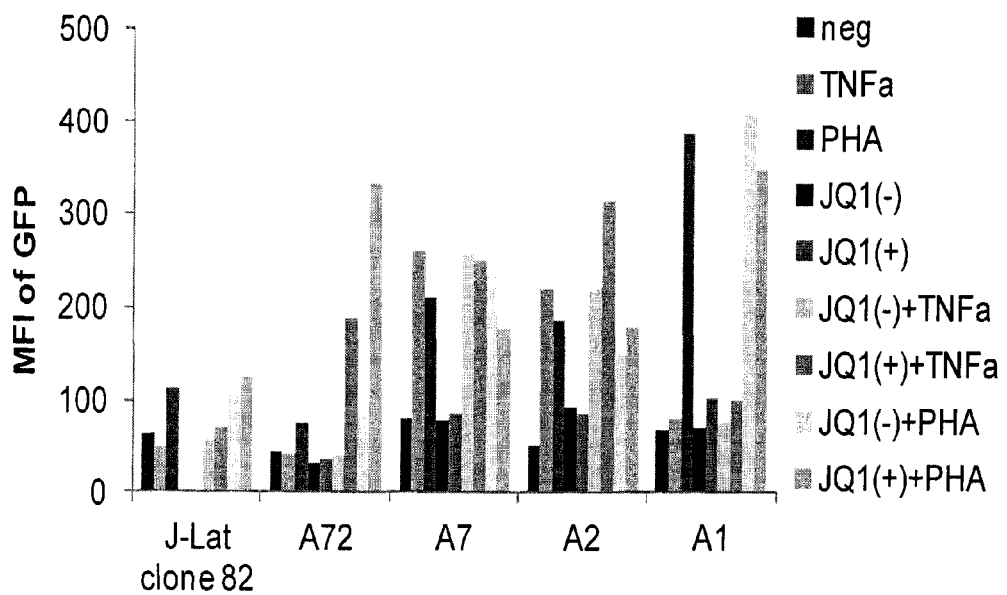
Figure 3D:
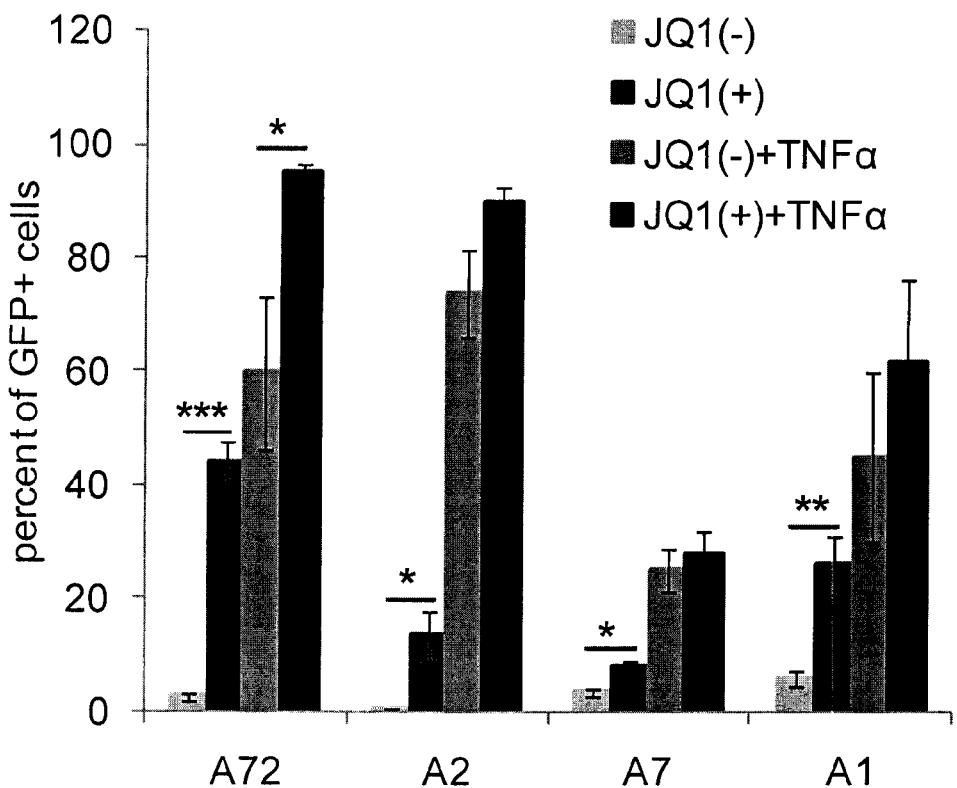
Figure 3E:
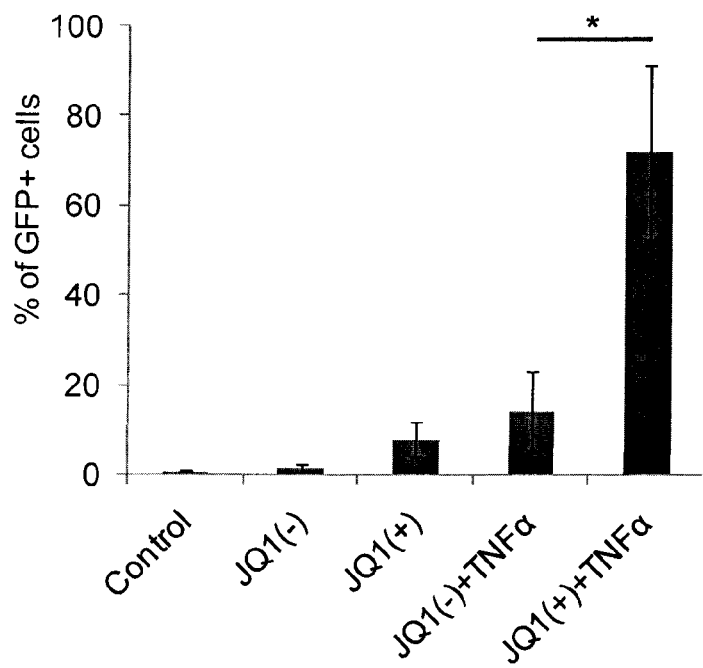
Figure 3F:
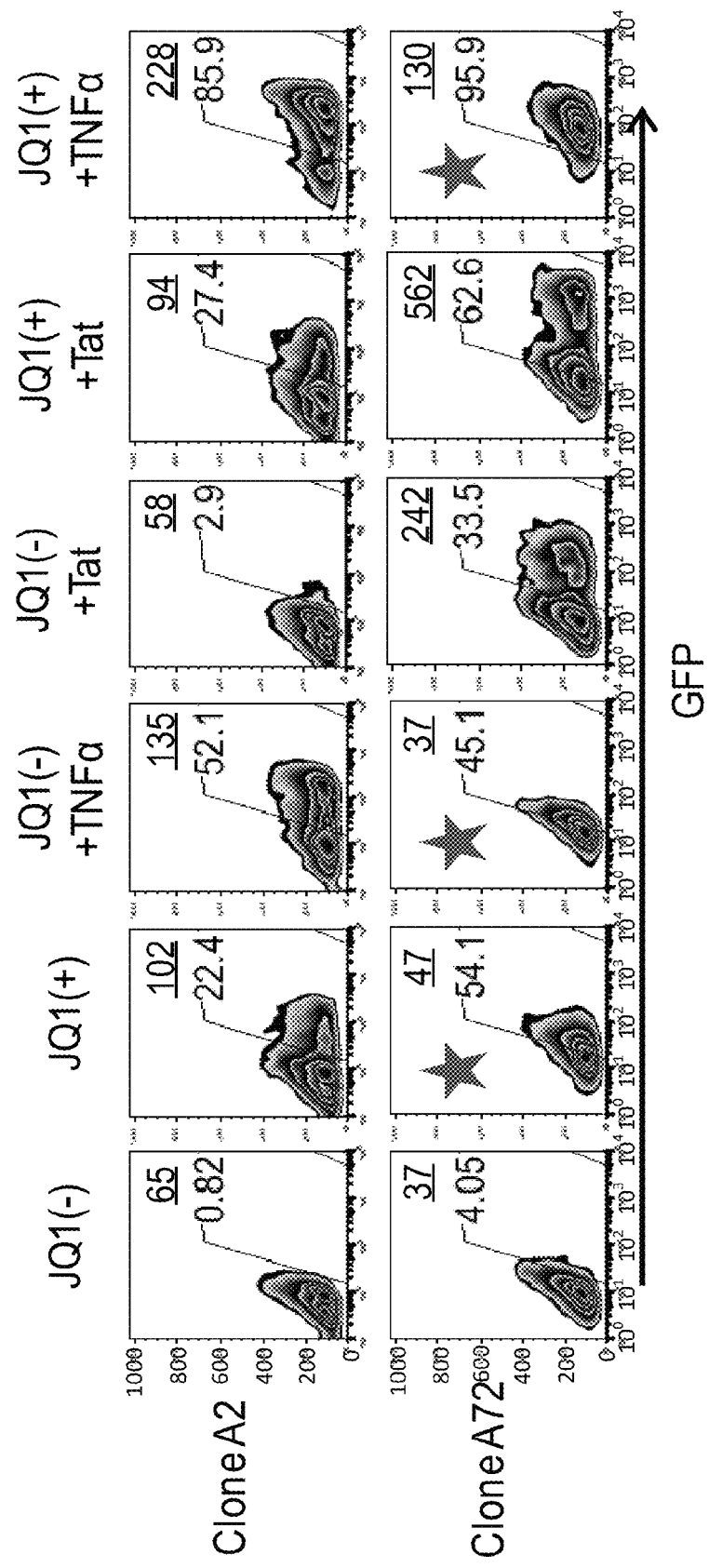

FIG. 3A shows that JQ1(+) drives reactivation of the HIV LTR in a latently infected cell line. The latently infected cell line, J-Lat clone A2, was reactivated with TNFα or PHA in the presence of inactive JQ1(−) or active JQ1(+) (0.5 µM) for 16 hours. GFP expression was measured by flow cytometry. FIGS. 3B and 3C shown the percentage of cells positive for GFP (FIG. 3B) and the mean MFI of GFP (FIG. 3C) in latently infected cell lines, J-Lat clones 82, A72, A7, A2, and A1, at 16 hours after TNFα or PHA was added in the cultures in the presence of JQ1(+) or JQ1(−). For FIG. 3D, latently infected Jurkat-derived cell lines, J-Lat A1, A2, A7, and A72, were reactivated with TNFα in the presence of an active enantiomer, JQ1(+) (1 µM), or an inactive control enantiomer, JQ1(−), for 16-18 hours. GFP expression in cells was measured by flow cytometry and is indicated as percent of GFP+ cells in gated live cell populations. An average of 5 experiments is shown. * p<0.05,  p<0.01, * p<0.001. FIG. 3E shows the percentage of GFP+ cells of CEMss LTR-GFP cells cultured with 20 ng/ml TNFα in the presence of JQ1(+) or JQ1(−) (1 µM) for 1 day (without Tat). Average of 3 experiments is shown. * p<0.05. For FIG. 3F, J-Lat A2 and A72 cells were reactivated with TNFα (20 ng/ml) or HIV Tat protein (50 µg/ml) in the presence of JQ1(+) or JQ1(−) for 16-18 hours, and GFP expression in cells was measured by flow cytometry. One representative experiment is shown. In each dot plot, non-underlined numbers indicate percentage of GFP+ cells and underlined numbers indicate mean fluorescence of GFP (MFI).

Figure 4:
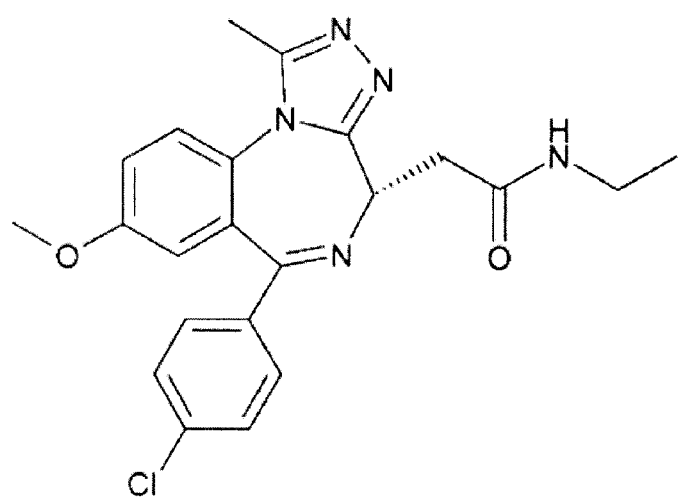
Figure 4:
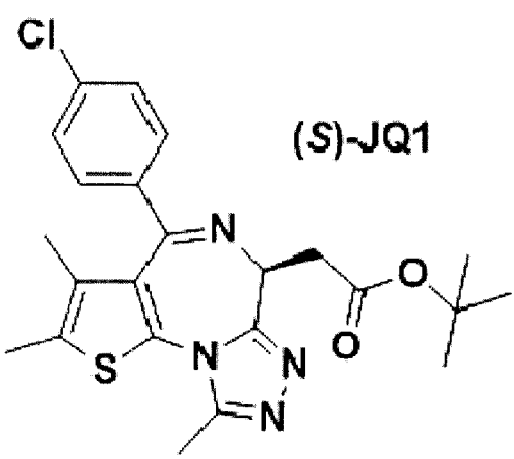
Figure 4:
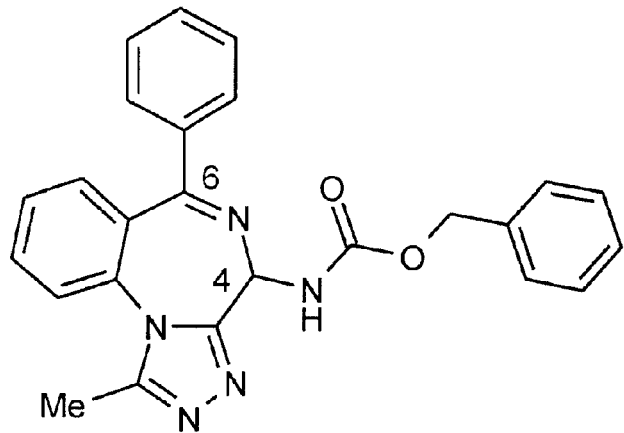

FIGS. 4A-4C provide the chemical structures of GSK525762A (I-BET) (FIG. 4A), JQ1 (tert-butyl 2-((6S)-4-(4-chlorophenyl)-2,3,9-trimethyl-6H-thieno[3,2-f][1,2,4]triazolo[4,3-a][1,4]diazepin-6-yl)acetate) (FIG. 4B), and GW841819X (FIG. 4C).

Figure 5A:
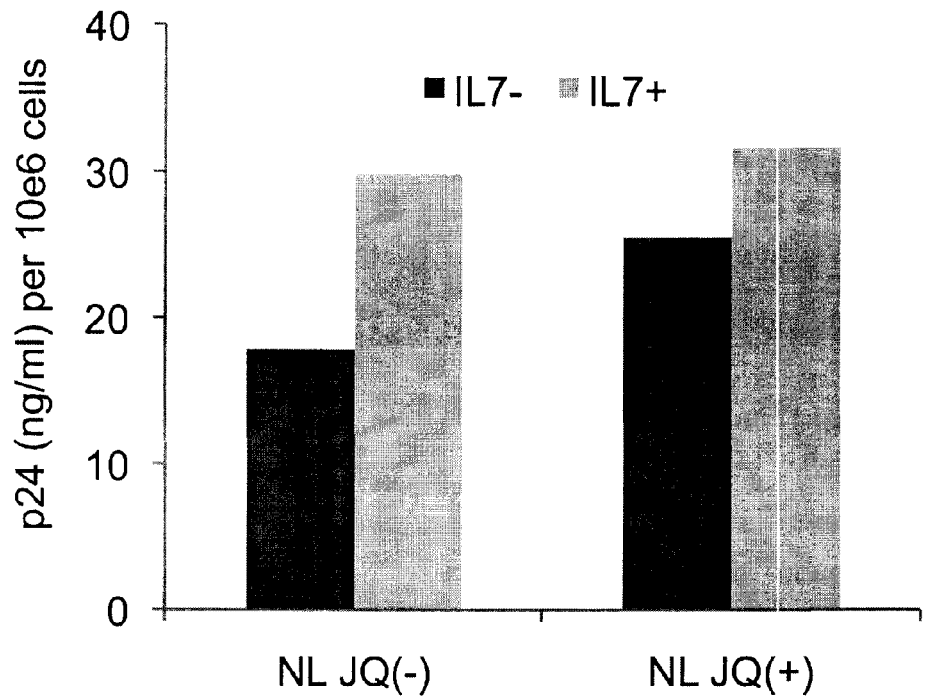
Figure 5B:
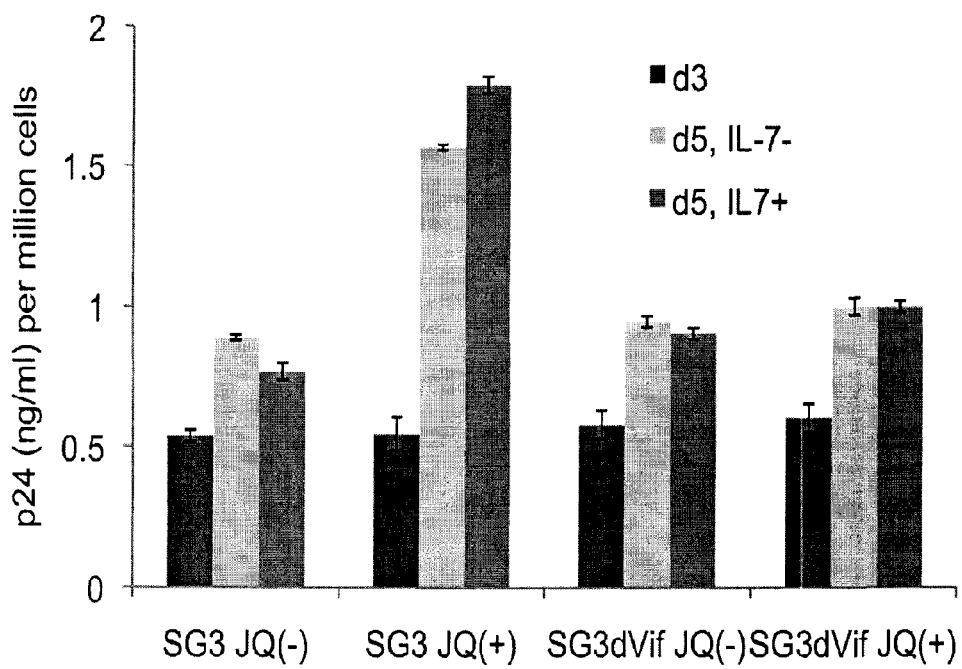

FIG. 5A shows p24 levels per million cells of primary resting CD4 T-cells spinoculated with HIV-1 NL43 and then cultured in the presence of 1 µM of JQ1(+) or JQ1(−) and, optionally, IL-7 (20 ng/ml; at day 3 after infection). A representative of three experiments is shown. FIG. 5B shows p24 levels per million cells of primary resting CD4 T-cells spinoculated with SG3 or SG3ΔVif (SG3dVif) and then cultured in the presence of 1 µM of JQ1(+) or JQ1(−) and, optionally, IL-7 (20 ng/ml; at day 3 after infection). AZT (100 µM) was added at day 1 after infection to prevent the spreading infection. The level of p24 in the media was measured by ELISA at day 3 (d3) and day 5 (d5) post-infection. The data shown are summarized for triplicate samples. JQ1(+) drives reactivation of the HIV LTR in wild-type SG3 latently infected cells, but not in SG3ΔVif infected cells.

Figure 6A:
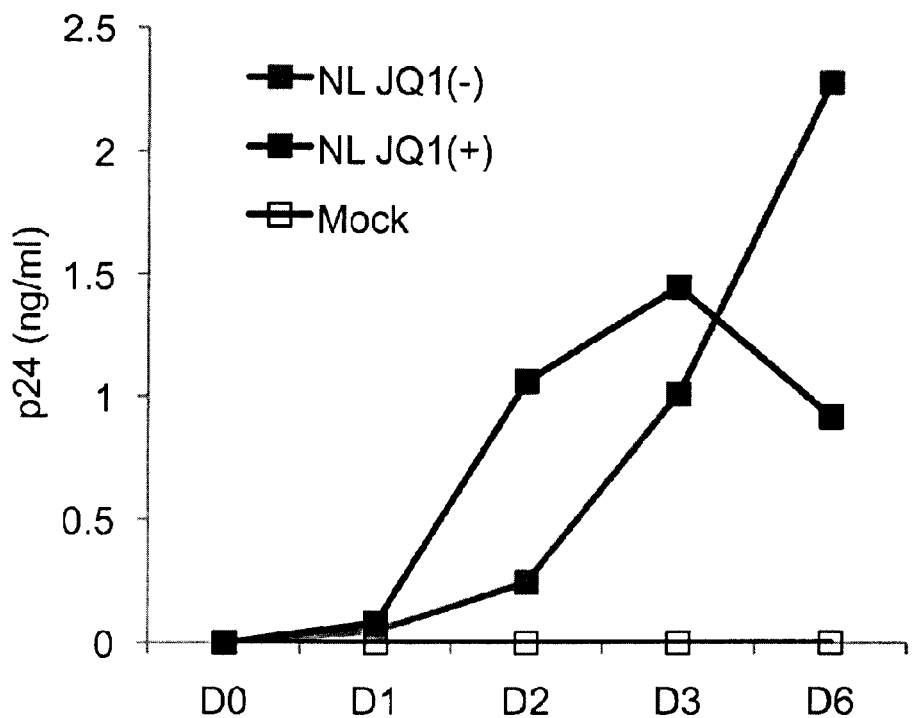
Figure 6B:
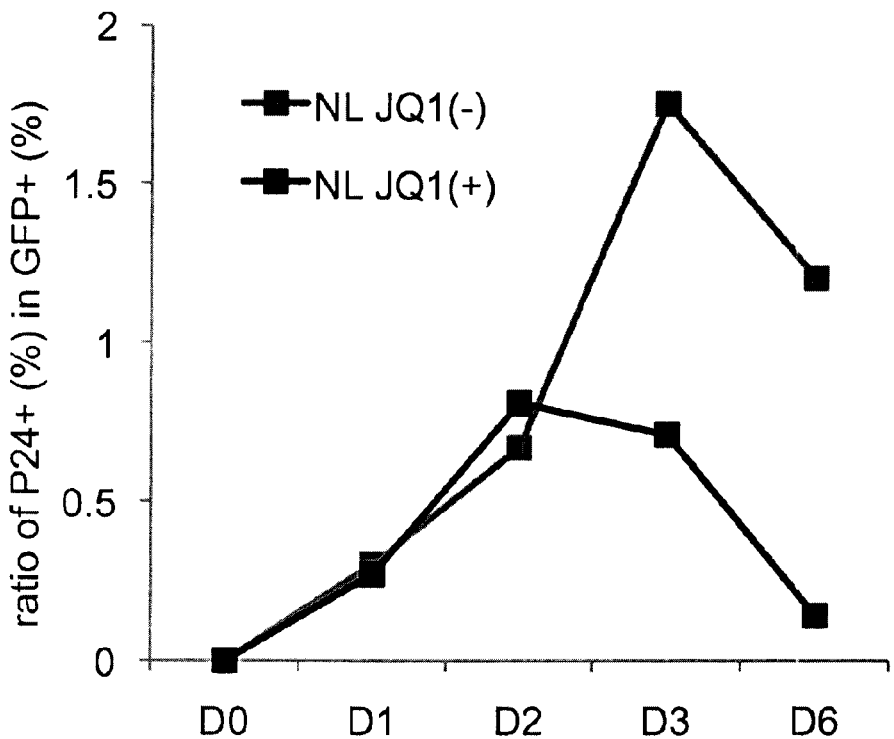
Figure 6C:
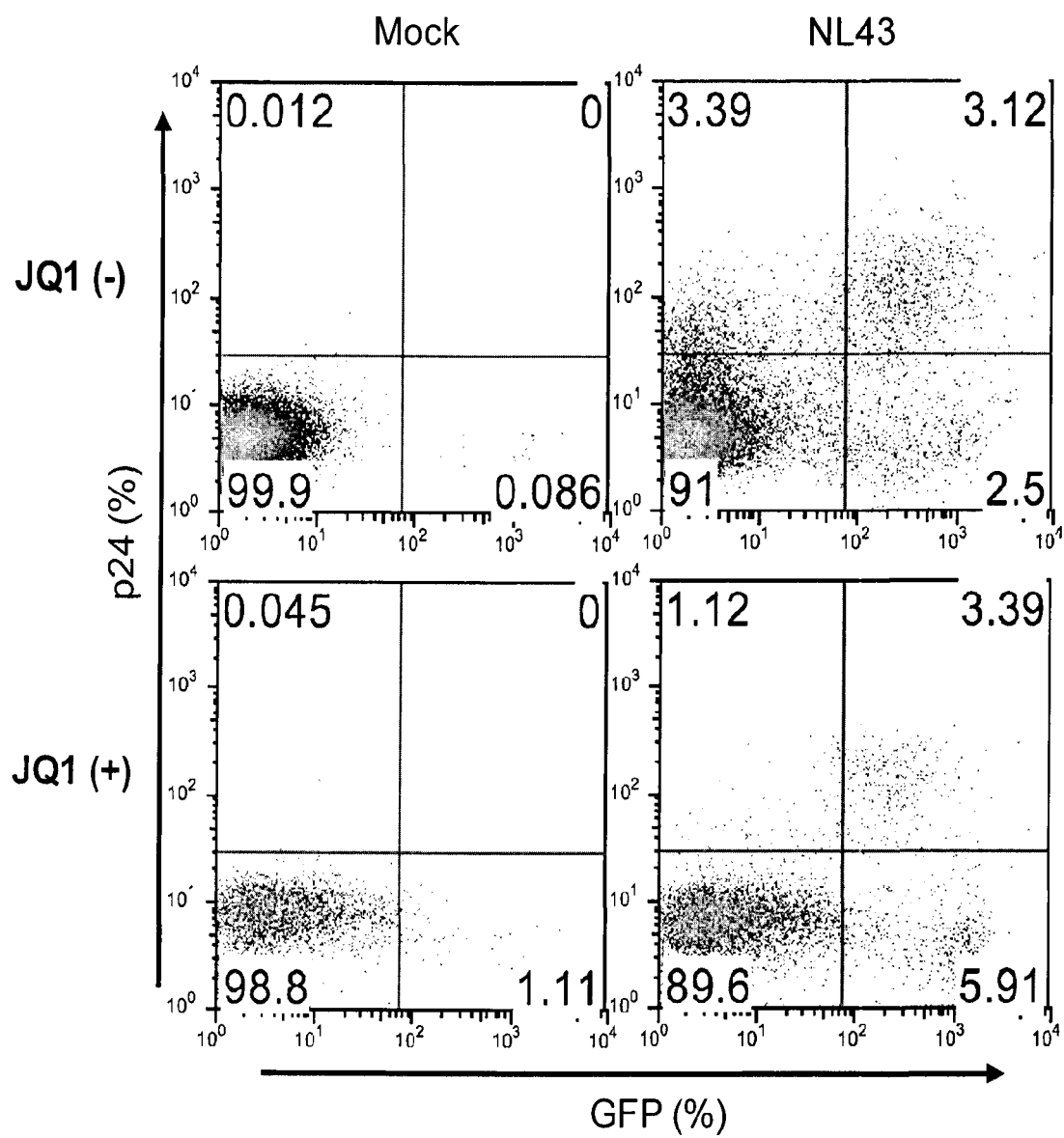

FIG. 6A provides a graph of p24Gag levels at various time points after the infection of CEMss LTR-GFP cells with NL43, which were cultured in the presence of JQ1(+) (1 µM) or JQ1(−). At various time points after infection, cell supernatants were collected and levels of p24Gag were measured by ELISA. A representative of three experiments is shown. FIG. 6B provides a graph of the ratio of percentage of P24+ cells in the GFP+ population. A representative of 2 experiments is shown. FIG. 6C shows GFP versus p24 staining of cells 3 days after infection.

Figure 7A:
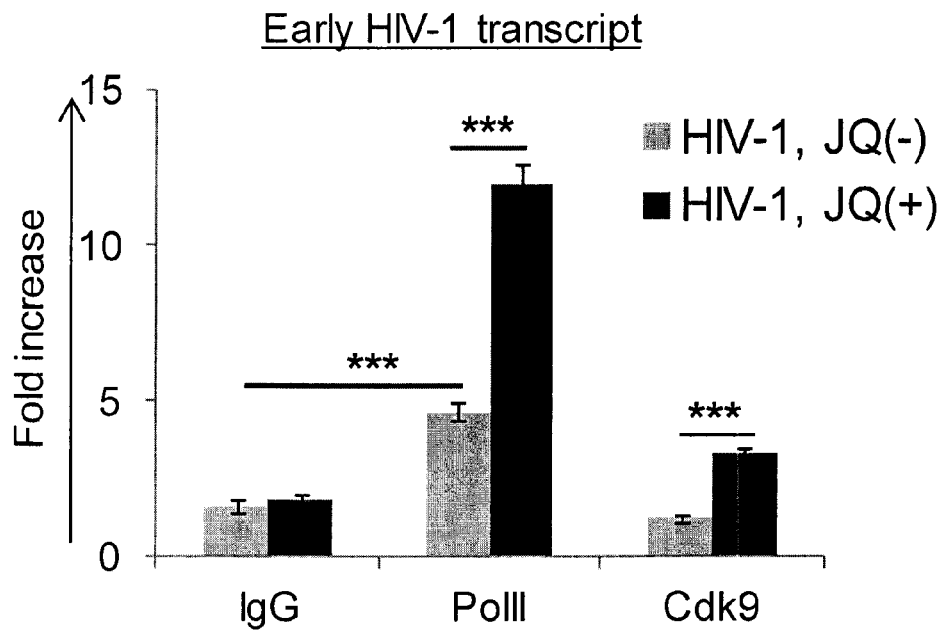
Figure 7B:
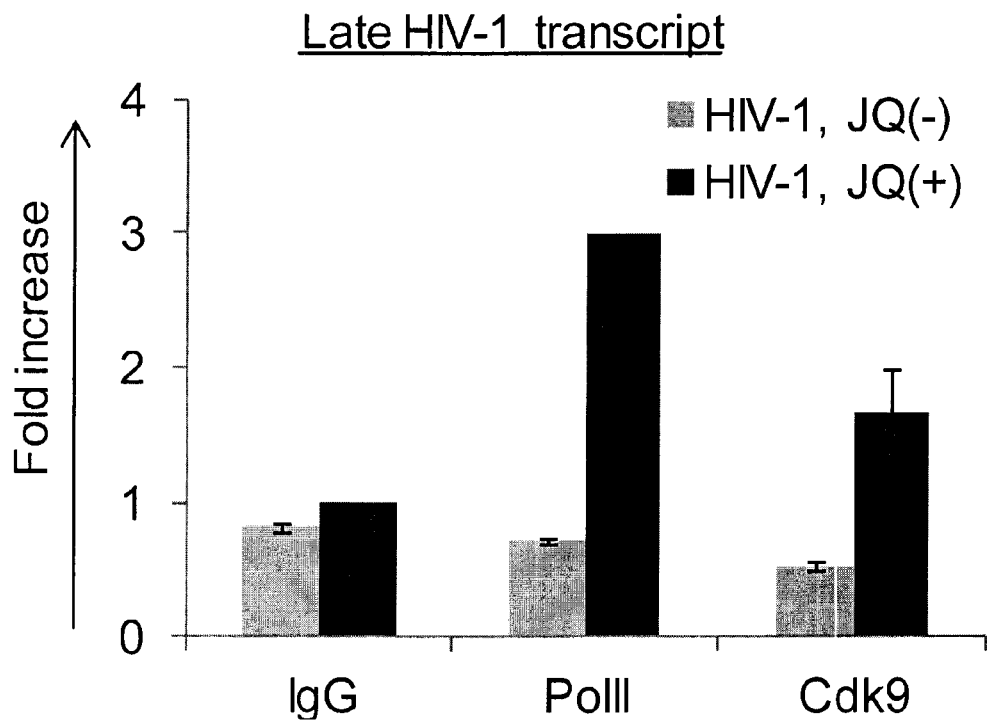

FIGS. 7A and 7B show the fold increase in the binding of IgG, RNA polymerase II, or Cdk9 to the HIV LTR in the presence of JQ1(+) or JQ1(−) for early (FIG. 7A) and late (FIG. 7B) HIV-1 transcript. ***p<0.001.

Figure 8:
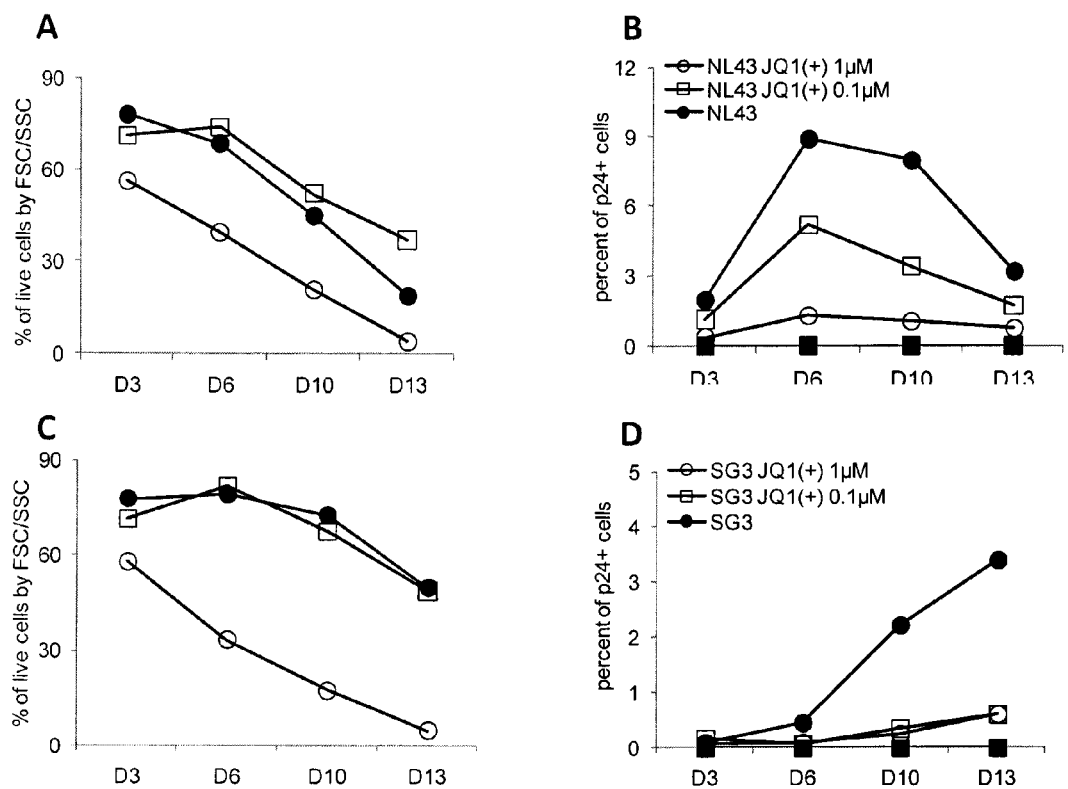

FIGS. 8A-8D show that JQ1 inhibits HIV production in the absence of JQ1-induced cell death. Primary CD4 T-cells were activated with anti-CD3/28, then infected with HIV, NL43 or SG3, and cultured in the presence of JQ1(+) (1 µM or 0.1 µM) or media. At days 3, 6, 10 and 13 after infection, cell death was measured by percent of FSC/SSC (forward scatter/side scatter) as indicated in individual plots (FIGS. 8A and 8C). The expression of p24 in live cells was examined by flow cytometry and is shown as the percentage of p24+ cells (FIGS. 8B and 8D).

Figure 9A:
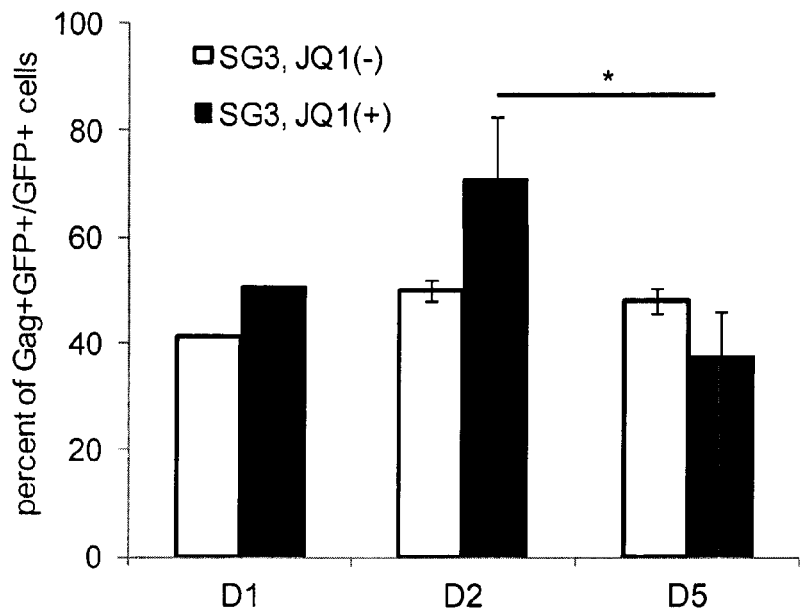
Figure 9B:
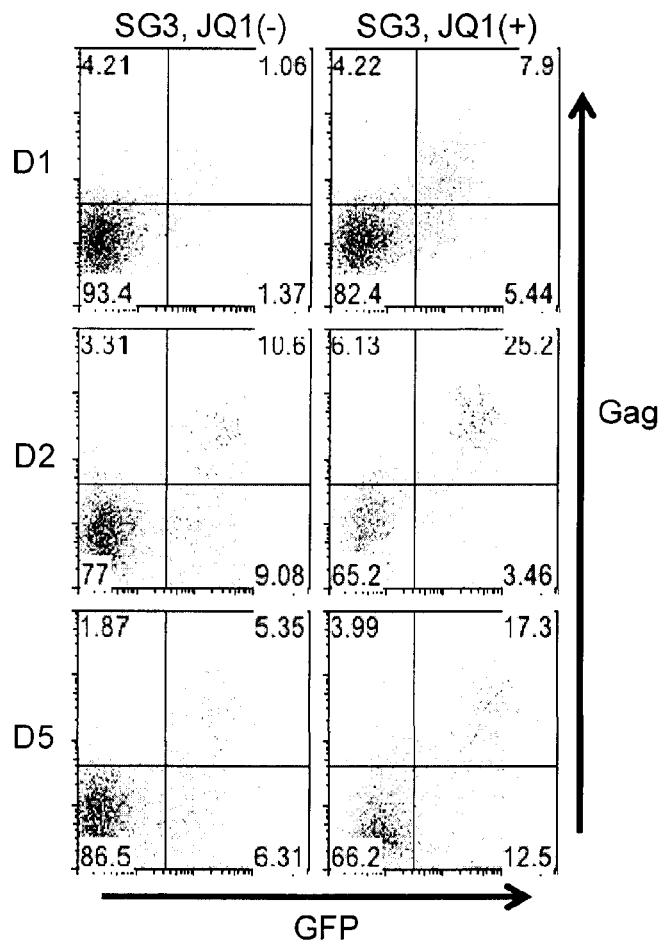

FIG. 9A provides a graph of the ratio of percentage of P24+ cells in the GFP+ population of CEMss LTR-GFP cells infected with SC3 and cultured in the presence of JQ(−) or JQ1(+) for 1, 2, and 5 days. FIG. 9B shows GFP versus p24 staining of cells 1, 2, or 5 days after infection.

DETAILED DESCRIPTION OF THE INVENTION

The present invention provides methods to treat, control, and/or cure retroviral infections using antagonists (e.g., cell-permeable small molecules) of cellular BET (Bromodomains and Extra Terminal) protein family. HIV Vif (viral infectivity factor) interacts with two cellular proteins, Brd4 and Cdk9, to drive cells out of G1 into the S phase of the cell cycle (Wang et al. (2011) Blood 117:1260-1269). Cdk9 is a component of the heterodimer p-TEFb (positive transcription elongation factor b). Brd4, a BET family member, acts by binding to acetylated lysines on histones and other nuclear factors to regulate gene expression. Brd4 recruits p-TEFb to promoters of active genes, altering gene transcription and thus stimulating progression from G1 to S. The HIV Tat protein also recruits p-TEFb to the viral LTR, a crucial step for efficient transcriptional elongation of HIV. Overexpression of Brd4 disrupts the interaction between Tat and p-TEFb and suppresses the ability of Tat to transactivate the HIV promoter (Bisgrove et al. (2007) PNAS 104:13690-13695).

The anti-HIV activity of BET antagonists is shown hereinbelow. Specifically, it is shown that BET antagonism inhibits viral replication and drives activation of the HIV LTR. The BET antagonists displace BET from chromatin by competitively binding to their acetylated lysine binding sites. As such, antagonism (e.g., with small molecule antagonists) of Brd4 and other BET proteins controls and cures an HIV infection. Based on work in other systems (e.g., bone marrow-derived macrophages), BET antagonists such as JQ1 may also inhibit inflammatory cytokine expression by activated T-cells in the presence or absence of infection. Accordingly, without being bound by theory, both effects of BET antagonism (i.e., inhibition of cytokine expression and the disruption of Brd4 function) may lead to the inhibition of viral replication.

The present invention encompasses methods for preventing, inhibiting, and/or treating a retroviral infection in an animal. In a particular embodiment, the method comprises administering at least one composition comprising at least one BET antagonist and at least one pharmaceutically acceptable carrier to an animal. The animal may be a mammal, particularly a primate or human. In a particular embodiment, the retrovirus is a lentivirus. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). The methods may further comprise the delivery of at least one anti-retroviral (e.g., an anti-HIV) compound before, after, and/or simultaneously with the BET antagonist(s). The methods may further comprise the delivery of at least one other activation (e.g., HIV activation) agent (e.g., protein kinase C activators (e.g., prostratin, bryostatin), histone deacetylase inhibitors (e.g., trichostatin A, valproic acid, sodium butyrate, vorinostat, romidepsin), TNFα, PHA, Tat, and/or IL-7).

The instant invention also encompasses methods for inhibiting and/or preventing a retroviral (e.g., HIV) infection, replication, and/or viral production. In a particular embodiment, the methods comprise delivering to a cell at least one BET antagonist (e.g., prior to or simultaneously with a retrovirus). The methods may further comprise the delivery of at least one anti-retroviral (e.g., an anti-HIV) compound before, after, and/or simultaneously with the BET antagonist(s). The methods may further comprise the delivery of at least one other activation agent. The methods may be performed in vitro (e.g., cell culture) or in vivo.

The instant invention also encompasses methods for inducing retroviral (e.g., HIV) activation. In a particular embodiment, the method comprises delivering at least one BET antagonist to a cell which is latently infected with a retrovirus. The methods may be performed in vitro (e.g., cell culture) or in vivo. The methods may further comprise the delivery of at least one other activation agent. The methods may also be used to screen for HIV therapeutic agents (e.g., those with synergistic effects with the BET antagonist) by further contacting the cells with a test compound and monitoring retrovirus levels/clearance (e.g., compared to in the absence of the test compound).

BET antagonists of the instant invention disrupt the function of BET proteins (e.g., Brd2, Brd3, Brd4). In a particular embodiment, the BET antagonist specifically disrupts the function of Brd4 (bromodomain containing protein 4; see, e.g., Gene ID: 23476). In a particular embodiment, the BET antagonist specifically binds the acetylated lysine (e.g., of acetylated histones) recognition pocket (e.g., within the bromodomain). In a particular embodiment, the BET antagonist is a small molecule inhibitor. Three synthetic BET antagonists that have been recently developed are JQ1, I-BET, and GW841819X (Nicodeme et al. (2010) Nature 468:1119-1123; Filippakopoulos et al. (2010) Nature 468:1067-1073; Gamsjaeger et al. (2011) Mol. Cell. Biol., 31:2632-2640). In another embodiment, the BET antagonist is an inhibitory nucleic acid molecule, such as an antisense or siRNA (see, e.g., brd4 siRNA from Dharmacon (Chicago, Ill.); brd4 siRNA from Chung et al., J. Med. Chem. (2011) 54:3827-3838 (page S20); and human analogs of the mouse brd4 siRNA provided in Nicodeme et al. (2010) Nature 468:1119-1123). Examples of small molecule BET antagonists include, without limitation, JQ1 (FIG. 4), I-BET (GSK525762A) (FIG. 4), GW841819X (FIG. 4; Chung et al., J. Med. Chem. (2011) 54:3827-3838), thienotriazolodiazepine compounds, those provided in U.S. Patent Application Publication No. 2010/0286127 (including, e.g., those of Formula (I) and compounds 1-18), derivatives of the compounds of Formula (I) in U.S. Patent Application Publication No. 2010/0286127 (e.g., wherein $R_3$ is hydrogen, wherein the thiophene ring is replaced with a six-membered ring (e.g., an aryl or benzyl group, optionally substituted with one or more $R_1$ and/or $R_2$ groups), and/or wherein $R_4$ is —$(CH_2)_a$—CO—O—$R_9$), and pharmaceutically acceptable salts thereof. In a particular embodiment, the BET antagonist is JQ1 or I-BET. In a particular embodiment, the BET antagonist is the JQ1(+) enantiomer. The JQ1(+) enantiomer need not be enantiomerically pure and may be in mixture with the JQ1(−) enantiomer, though it is preferable to have a composition comprising substantially pure JQ1(+) enantiomer.

The compositions of the instant invention can be administered to an animal, in particular a mammal, more particularly a human, in order to treat/inhibit/prevent a retroviral infection (e.g., the composition may be administered before, during, or after a retroviral infection). The pharmaceutical compositions of the instant invention may also comprise at least one other antiretroviral agent (e.g., an anti-HIV agent). The additional antiretroviral agent may also be administered in a separate composition from the BET antagonists of the instant invention. The compositions may be administered at the same time or at different times (e.g., sequentially (e.g., the BET antagonists may be administered prior to, after, or simultaneously with the antiretroviral agents)). In a particular embodiment of the instant invention, the BET antagonists are administered with (e.g., before, during, and/or after) highly active antiretroviral therapy (HAART).

The compositions of the instant invention may be administered, in a therapeutically effective amount, to a patient in need thereof. The pharmaceutical compositions of the present invention can be administered by any suitable route, for example, by injection (e.g., parenteral, intramuscular, intravenous, or intraperitoneal administration), by oral, pulmonary (e.g., intratraechially), nasal, topical, or other modes of administration such as controlled release devices. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween™ 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science and Practice of Pharmacy" by Alfonso R. Gennaro (Lippincott Williams & Wilkins) which are herein incorporated by reference. The pharmaceutical composition of the present invention can be prepared, for example, in liquid form, aerosolized form, or can be in pill or dried powder form (e.g., lyophilized). The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Medical Applications of Controlled Release, Langer and Wise (eds.), CRC Press; Sefton, CRC Crit. Ref. Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press; Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105).

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The dosage ranges for the administration of the compositions of the invention are those large enough to produce the desired effect (e.g., curing, relieving, treating, and/or preventing the disease, disorder, or infection and/or the symptoms associated therewith). The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

In accordance with the present invention, the appropriate dosage unit for the administration of compositions of the instant invention may be determined by evaluating the toxicity of the molecules or cells in animal models. Various concentrations of agents in pharmaceutical preparations may be administered to animals, and the minimal and maximal dosages may be determined based on the beneficial results and side effects observed as a result of the treatment. Appropriate dosage unit may also be determined by assessing the efficacy of the agent treatment in combination with other standard drugs. The dosage units of the compositions may be determined individually or in combination with each treatment according to the effect detected.

The pharmaceutical preparation comprising the agents of the instant invention may be administered at appropriate intervals, for example, at least once or twice a day or more. The appropriate interval in a particular case would normally depend on the condition of the patient.

DEFINITIONS

The term "substantially pure" refers to a preparation comprising at least 50-60% by weight of a given material (e.g., nucleic acid, oligonucleotide, protein, peptide, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells.

The phrase "effective amount" refers to that amount of therapeutic agent that results in an improvement in the patient's condition.

The term "inhibit" in the context of inhibiting an HIV infection may refer to the reduction in the incidence of or the symptoms of the HIV infection being treated or the presence or extent of the HIV infection being treated.

As used herein, the term "prevent" refers to the prophylactic treatment of a subject who is at risk of developing a condition resulting in a decrease (e.g., at least a significant decrease) in the probability that the subject will develop the condition.

A "carrier" refers to, for example, a diluent, adjuvant, excipient, auxillary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in, e.g., "Remington's Pharmaceutical Sciences" (Ed. Gennaro; Mack Publishing, Easton, Pa.) and "Remington: The Science and Practice of Pharmacy" (Ed. Troy; Lippincott Williams & Wilkins, Baltimore, Md.).

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, an "anti-HIV compound" is a compound which inhibits HIV. Examples of an anti-HIV compound include, without limitation:

(I) nucleoside-analog reverse transcriptase inhibitors (NR-TIs; e.g., AZT (zidovudine, RETROVIR®), lamivudine (3TC, EPIVIR®), emtricitabine (EMTRIVA®), dideoxycytidine (ddC, zalcitabine, HIVID®), 2',3'-dideoxyinosine (ddI, VIDEX®), tenofovir DF (VIREAD®), stavudine (d4T, ZERIT®), abacavir (1592U89; ZIAGEN®), adefovir dipivoxil (bis(POM)-PMEA; PREVON®), lobucavir (BMS-180194), BCH-10652, emitricitabine, elvucitabine, and lodenosine (FddA; 2'-beta-fluoro-2',3'-dideoxyadenosine)), trizivir (abacavir, zidovudine, and lamivudine), (II) non-nucleoside reverse transcriptase inhibitors (NNR-TIs; e.g., delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), DAPY (TMC120), BILR-355 BS, PHI-236, and PHI-443 (TMC-278)), (III) protease inhibitors (PIs; e.g., amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515), Kaletra™ (lopinavir and ritonavir), and (IV) fusion inhibitors (FIs; e.g., T-20 (DP-178, FUZEON®) and T-1249).

As used herein, the term "nucleoside-analog reverse transcriptase inhibitors" (NRTIs) refers to nucleosides and nucleotides and analogues thereof that inhibit the activity of HIV-1 reverse transcriptase. As used herein, NNRTIs are allosteric inhibitors which bind reversibly at a nonsubstrate-binding site on the HIV reverse transcriptase, thereby altering the shape of the active site or blocking polymerase activity. As used herein, the term "protease inhibitor" refers to inhibitors of the HIV-1 protease. As used herein, "fusion inhibitors" are compounds, such as peptides, which act by binding to HIV envelope protein and blocking the structural changes necessary for the virus to fuse with the host cell.

Anti-HIV compounds also include HIV vaccines such as, without limitation, ALVAC® HIV (vCP1521), AIDSVAX®B/E (gp120), and combinations thereof. Anti-HIV compounds also include HIV antibodies (e.g., antibodies against gp120 or gp41 (e.g., VCR01 (Zhou et al. (Science (2010) 329:811-7), PG9 and PG16 (Doores et al. (J. Virol. (2010) 84:10510-21), and see also Walker et al. (Science (2009) 326:285-9), particularly broadly neutralizing antibodies. Other anti-HIV agents include, without limitation, recombinant soluble CD4 (rsCD4), an anti-CD4 antibody (e.g., from Tanox, Inc.), an anti-CCR5 antibody (e.g., Pro 140); a CXCR4 blocker (e.g., AMD 3100), an HIV entry inhibitor (e.g., Pro-542; Progenies), and a CCR5 blocker (e.g., SCH-C, SCH-D; Schering Plough).

As used herein, the term "highly active antiretroviral therapy" (HAART) refers to HIV therapy with various combinations (e.g., at least three) of therapeutics such as nucleoside reverse transcriptase inhibitors, non-nucleoside reverse transcriptase inhibitors, HIV protease inhibitors, and fusion inhibitors. For example, HAART may include two reverse transcriptase inhibitors and a protease inhibitor.

As used herein, the terms "activation agent" of "HIV activation agent" refer to compounds that stimulate proviral latent DNA to begin transcription, replication, and/or production of infectious virus and/or cell surface antigens.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences separated by a small loop sequence wherein one of the sequences is complimentary to the gene target. shRNA molecules are typically processed into an siRNA within the cell by endonucleases. Exemplary modifications to siRNA molecules are provided in U.S. Application Publication No. 20050032733. Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

The following examples describe illustrative methods of practicing the instant invention and are not intended to limit the scope of the invention in any way.

EXAMPLE 1

It is shown herein that HIV infections can be inhibited, controlled, and/or cured using cell-permeable small molecule antagonists of cellular BET family proteins. It is demonstrated hereinbelow that BET antagonism inhibits virus production (FIG. 1) and drives activation of the HIV LTR (FIGS. 2 & 3).

BET antagonists inhibit viral infection in primary activated CD4 T-cells. Specifically, the effect of the BET antagonist JQ1(+) on viral replication was tested in HIV-infected T-cells. Primary activated CD4 T-cells were infected with X4-tropic virus (NL43 or SG3) or R5-tropic virus (BAL1 or BL2) in the presence or absence of JQ1(+) (1 µM). Viral infection was measured by flow cytometry or ELISA at various days after infection. Levels of infection were found to decrease in the presence of the BET antagonist, but not with DMSO or a control enantiomer JQ1(−) (FIG. 1). JQ1 significantly inhibited HIV infection (*p<0.05) in primary CD4 T-cells at days 3 and 6 after infection (FIG. 1B). The inhibition of viral infection was also observed with 0.1 µM of JQ1 (FIG. 1C). These data indicate that BET antagonists inhibit HIV infection. Notably, at day 6 after infection, production of p24 decreased below control values in supernatants of JQ1(+) containing cultures (FIG. 1D), despite the fact that cells continued to express high levels of GFP (FIG. 2A). These data indicate that JQ1 promotes LTR activation, while inhibiting viral production at late time points following infection.

BET antagonists also drive activation of the HIV LTR. Specifically, the effects of JQ1 on transcription from the HIV LTR were tested. CEMss LTR-GFP cells (a reporter cell line stably transfected with GFP under the control of the HIV-1 LTR promoter) were infected with NL43 and cultured in the presence of BET antagonists or controls. GFP expression was measured at days 0, 1, 2, 3, and 6 post-infection. GFP expression was higher in the presence of the BET inhibitor (JQ1) compared to controls (FIG. 2A). Further, by varying the amount of JQ1, it was determined that 0.25 µM of JQ1(+) was sufficient to dramatically increase Tat-driven HIV-1 transcription (FIG. 2B). CEMss LTR-GFP cells were also cultured in the presence of JQ1(+) or JQ1(−) (1 µM) and different amount of HIV-1 Tat (0-32 µg/ml). FIGS. 2C and 2D show that 8 µg/ml of HIV-1 Tat alone activated the express of GFP (FIG. 2C) while the mean fluorescence intensities (MFI) of GFP was dramatically enhanced at 8, 16, or 32 µg/ml of Tat in the presence of JQ1(+) (FIG. 2D). FIG. 2E provides dot plots of the experiments.

Next, the effect of JQ1 on activation of the HIV LTR was tested using a latently infected Jurkat-derived cell clone, J-Lat clone A2. GFP expression in J-Lat clone A2 is induced upon reactivation with tumor necrosis factor-alpha (TNFα) or phytohaemagglutinin (PHA). It was determined that GFP expression (% positive cells and mean fluorescence intensity) was higher in cells cultured with TNFα or PHA plus JQ1(+) than with the JQ1(−) control compound (FIG. 3A), indicating that JQ1 drives reactivation of the HIV LTR in latently infected cells. FIGS. 3B and 3C also show that JQ1(+) drives the reactivation of the HIV LTR in latently infected cell lines, J-Lat clones 82, A72, A7, A2, and A1, as determined by GFP expression (% positive cells (FIG. 3C) and mean fluorescence intensity (FIG. 3D)). FIG. 3E further demonstrates that JQ1 promotes TNFα-induced activation of the HIV LTR in CEMss LTR-GFP cells in the absence of Tat.

FIG. 5 shows that JQ1(+) drives the reactivation of the HIV LTR in latently infected primary resting CD4 T-cells. For FIG. 5A, primary resting CD4 T-cells were purified and spinoculated with HIV-1 NL43 or mock control. The infected cells were then cultured in the presence of 1 μM of JQ1(+) or JQ1(−). At day 3 after infection, IL-7 (20 ng/ml) was added in some of the cultures. Cells were counted and cell supernatants were collected at day 5 after infection. The level of p24Gag in the media was measured by ELISA and p24 levels per million cells are shown in FIG. 5A. For FIG. 5B, primary CD4 T-cells were spinoculated with SG3 or SG3deltaVif and cultured in the presence of 1 μM of JQ1(+) or JQ1(−). AZT (100 μM) was added at day 1 after infection to prevent the spreading infection. IL7 (20 ng/ml) was added in some culture at day 3 after infection and the level of p24 in the media was measured by ELISA at day 3 and day 5 post-infection. The data shown are summarized with triplicates. FIG. 5B shows that JQ1(+) drives the reactivation of the HIV LTR in wild-type SG3 latently infected cells, but not in SG3deltaVif infected cells.

To determine if JQ1(+) affects viral integration in primary resting CD4 T-cells, the cells were purified and infected with HIV-1 NL43 or mock control. The infected cells were then cultured in the presence of 1 μM of JQ1(+) or JQ1(−) for 48 hours. Cell pellets were collected at 0 hours and 48 hours after infection. DNA was isolated and the viral integration in resting CD4 T-cells was measured by Alu-PCR. As seen in Table 1, JQ1(+) does not significantly affect the viral integration in primary resting CD4 T-cells.

TABLE 1

| | JQ1(+) does not affect viral integration in primary resting CD4 T-cells. | | |
|---|---|---|---|
| provirus/cell | T0 h | T48 h, JQ(−) | T48 h, JQ(+) |
| Exp. 1 | 0.002 ± 0.0002 | 0.527 ± 0.064 | 0.559 ± 0.005 |
| Exp. 2 | 0 | 0.400 ± 0.0009 | 0.444 ± 0.120 |

As seen in FIG. 6, the Brd4 antagonist, JQ1(+), decreases the viral production of HIV-1 at the later time point of infection in activated primary CD4 T-cells or CEMss LTR-GFP cell lines. Without being bound by theory, this decrease in viral production may be due to 1) JQ1(+) causing G1 arrest in the cell cycle, resulting in cell death or affecting the cell fitness that contributes to the overall decreased viral production; and/or 2) JQ1(+) affecting other viral or host cellular proteins' transcriptions, thereby leading to the decreased packaging of viral particles.

FIG. 6A shows that viral production was decreased in the presence of JQ1(+) at day 6 after infection. Specifically, CEMss LTR-GFP cells were infected with NL43 and cultured in the presence of BET antagonist, JQ1(+) (1 μM) or a control JQ1 enantiomer, JQ1(−). At various time points after infection, cell supernatants were collected and the levels of p24Gag was measured by ELISA. FIGS. 6B and 6C show that the expression of p24Gag in the infected cells was decreased at day 3 after infection. The experiments were done as shown in FIG. 6A and the cells were stained for the expressions of GFP and p24-PE at day 1, 2, 3, and 6 after infection. FIG. 6B provides a graph of the ratio of p24$^+$ in the GFP+ population. A representative of two experiments is shown. FIG. 6C shows a representative of GFP and p24-phycoerythrin (PE) staining at day 3 after infection.

EXAMPLE 2

To further study the mechanism of how JQ1 drives reactivation of HIV latency, HIV latently infected T-cell lines—J-Lat clones A1, A2, A7, and A72—were utilized. The effect of JQ1(+) on reactivation of HIV latency in these cell lines were confirmed. TNFα (20 ng/ml) or PHA (1.5 μg/ml) was added to cultures of J-Lat clones in the presence of 1 μM JQ1(+) or JQ1(−). After 16 hours, expression of GFP was measured by flow cytometry. TNFα or PHA induced GFP expression, indicating that TNFα reactivated HIV latently infected cells. In the presence of HIV Tat, BET antagonism enhances Tat-driven transcription of the HIV LTR in J-Lat clones A2 and A72 (FIG. 3F; underlined numbers indicate mean GFP fluorescence, non-underlined numbers indicate percent of GFP+ cells). This result is consistent with the findings that overexpression of Brd4 suppresses the ability of Tat to transactivate the HIV promoter. Importantly, JQ1(+) alone also increased the percent of cells expressing GFP (FIG. 3D), indicating that JQ1 reactivates the HIV LTR. Interestingly, when cells were cultured with both TNFα (20 ng/ml) and JQ1(+), GFP expression is dramatically enhanced in J-Lat clones A72 and A2 (FIG. 3D), indicating that JQ1(+) increases TNFα-induced HIV transcription in vitro. Displacement of Brd4 from chromatin by JQ1(+) may cause conformational change in the chromatin, exposing NF-κb binding sites, leading to increased HIV transcription and reactivation of latency.

To further investigate the mechanism of JQ1(+) reactivation of HIV transcription in latently infected T-cells, the binding of RNA polymerase II (Pol II) and p-TEFb (Cdk9/Cyclin T) to the promoter region of HIV LTR was measured using chromatin immunoprecipitation (ChIP). A CEMss reporter cell line stably transfected with GFP under the control of the HIV LTR promoter was used. CEMss LTR-GFP cells were infected with HIV NL4-3 in the presence of JQ1(+) or JQ1(−). At days 3 to 5 of infection, cells were collected and sheared, and formaldehyde cross-linked chromatin extracts were immunoprecipitated with antibodies specific for IgG, RNA polymerase II, or Cdk9. The abundance of HIV LTR DNA in immunoprecipitates was assessed by qPCR with two sets of primers specific for early or late regions of the HIV LTR. Binding of RNA Pol II to the HIV LTR was dramatically increased in HIV infected cells (FIGS. 7A and 7B, gray bar in Pol II group vs. gray bar in IgG group, *p<0.001). In the presence of JQ1(+), the binding of RNA Pol II and Cdk9 to the HIV LTR was significantly increased, when compared to cultures with JQ1(−) (FIGS. 7A and 7B, dark bars vs. gray bars in Pol II or Cdk9 groups, **p<0.001). This indicates that JQ1(+) promotes HIV transcription by increasing the binding of RNA polymerase II and Cdk9 to the HIV LTR.

In an effort to determine whether the inhibition of HIV production by JQ1 was due solely to JQ1(+) induced cell death, the experiments were repeated with a concentration of JQ1(+) (0.1 μM) that did not cause cell death above control values (FIGS. 8A and 8C, open squares). As shown in FIGS. 8B and 8D, this low concentration of JQ1(+) still suppressed the relative number of virus-expressing cells (FIGS. 8B and 8D, open squares). Of note, mean fluorescence of p24 was unchanged in the presence of the active inhibitor, indicating there was not a non-specific toxic drug effect and supporting the observation that BET antagonism inhibits HIV production at late time points of infection in primary activated CD4 T-cells.

JQ1 induces decreased expression of HIV Gag in HIV-infected CEMss LTR-GFP cells at late time points of infection. As shown in FIG. 9A, levels of soluble p24 were decreased at day 6 post-infection in the T-cell line, CEMss LTR-GFP. The expression of Gag was measured in infected cells by flow cytometry. CEMss LTR-GFP cells were infected with SG3 and cultured in the presence or absence of JQ1(+). At 1-5 days post-infection, cells were stained for Gag by flow cytometry. The relative number of Gag-expressing live GFP+ cells was significantly decreased in the presence of JQ1(+), but not JQ1(−), at day 5 post-infection (FIGS. 9A and 9B).

This result indicates that BET antagonism promotes LTR transcription, while inhibiting Gag, in cells at the late time points of infection. JQ1 may regulate the transcription of other host proteins involved in the translocation or packaging of Gag, which may contribute to decreased production of viral particles at late time points of infection (FIG. 9).

Certain of the above experiments were at least partly funded by a grant from the Bill & Melinda Gates Foundation through the Grand Challenges Explorations initiative.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating or inhibiting an HIV infection in a subject in need thereof, said method comprising administering to said subject a composition comprising at least one bromodomain containing protein 4 (Brd4) antagonist and at least one pharmaceutical carrier, wherein said Brd4 antagonist is a small molecule which specifically binds the acetylated lysine binding domain of said Brd4.

2. The method of claim 1, wherein said Brd4 antagonist is JQ1(+) or I-BET.

3. The method of claim 1, further comprising the administration of at least one additional anti-HIV compound.

4. The method of claim 3, further comprising the administration of highly active antiretroviral therapy to said subject.

5. The method of claim 1, further comprising the administration of at least one additional activation agent.

6. The method of claim 5, wherein said additional activation agent is selected from the group consisting of protein kinase C activators, histone deacetylase inhibitors, TNFα, PHA, Tat, and IL-7.

7. A method for inducing HIV reactivation, said method comprising delivering at least one bromodomain containing protein 4 (Brd4) antagonist to a cell which is latently infected with HIV,
wherein said Brd4 antagonist is a small molecule which specifically binds the acetylated lysine binding domain of said Brd4.

8. The method of claim 7, wherein said Brd4 antagonist is JQ1(+) or I-BET.

9. The method of claim 7, further comprising the administration of at least one additional anti-HIV compound.

10. The method of claim 9, further comprising the administration of highly active antiretroviral therapy to said cell.

11. The method of claim 7, further comprising the administration of at least one additional activation agent.

12. The method of claim 11, wherein said additional activation agent is selected from the group consisting of protein kinase C activators, histone deacetylase inhibitors, TNFα, PHA, Tat, and IL-7.

13. A method for inhibiting the infection of a cell by HIV, said method comprising delivering at least one bromodomain containing protein 4 (Brd4) antagonist to said cell,
wherein said Brd4 antagonist is a small molecule which specifically binds the acetylated lysine binding domain of said Brd4.

14. The method of claim 13, wherein said Brd4 antagonist is JQ1(+) or I-BET.

15. The method of claim 13, further comprising the administration of at least one additional anti-HIV compound.

16. The method of claim 15, further comprising the administration of highly active antiretroviral therapy to said cell.

17. The method of claim 13, further comprising the administration of at least one additional activation agent.

18. The method of claim 17, wherein said additional activation agent is selected from the group consisting of protein kinase C activators, histone deacetylase inhibitors, TNFα, PHA, Tat, and IL-7.

* * * * *